United States Patent
Joerger et al.

(10) Patent No.: US 10,758,154 B2
(45) Date of Patent: Sep. 1, 2020

(54) METHOD FOR OPERATING AN IMAGE SYSTEM OF A MEDICAL IMAGING MODALITY AND MEDICAL IMAGING MODALITY

(71) Applicant: SIEMENS HEALTHCARE GMBH, Erlangen (DE)

(72) Inventors: Clemens Joerger, Forchheim (DE); Gudrun Roth-Ganter, Ratshausen (DE)

(73) Assignee: Siemens Healthcare GmbH, Erlangen (DE)

( * ) Notice: Subject to any disclaimer, the term of this patent is extended or adjusted under 35 U.S.C. 154(b) by 474 days.

(21) Appl. No.: 15/381,381

(22) Filed: Dec. 16, 2016

(65) Prior Publication Data
US 2017/0177387 A1    Jun. 22, 2017

(30) Foreign Application Priority Data

Dec. 17, 2015  (DE) .......................... 10 2015 225 543

(51) Int. Cl.

| | |
|---|---|
| *A61B 8/00* | (2006.01) |
| *A61B 5/055* | (2006.01) |
| *G06F 9/451* | (2018.01) |
| *G06F 3/0484* | (2013.01) |
| *A61B 5/00* | (2006.01) |
| *A61B 6/03* | (2006.01) |
| *A61B 6/00* | (2006.01) |
| *G06F 3/0482* | (2013.01) |
| *G06F 19/00* | (2018.01) |

(52) U.S. Cl.
CPC .............. *A61B 5/055* (2013.01); *A61B 5/742* (2013.01); *A61B 5/7475* (2013.01); *A61B 6/032* (2013.01); *A61B 6/4441* (2013.01); *A61B 6/487* (2013.01); *G06F 3/0482* (2013.01); *G06F 3/0484* (2013.01); *G06F 3/04847* (2013.01); *G06F 9/453* (2018.02); *G06F 19/321* (2013.01); *A61B 6/461* (2013.01); *A61B 6/467* (2013.01)

(58) Field of Classification Search
CPC combination set(s) only.
See application file for complete search history.

(56) References Cited

U.S. PATENT DOCUMENTS

| | | | |
|---|---|---|---|
| 6,904,161 B1 | 6/2005 | Becker et al. | |
| 2006/0072700 A1 | 4/2006 | Chen et al. | |
| 2007/0239012 A1* | 10/2007 | Boeing ................. | A61B 6/032 600/439 |
| 2009/0171184 A1* | 7/2009 | Jenkins ................. | A61B 5/055 600/411 |
| 2011/0263980 A1 | 10/2011 | Mills et al. | |

FOREIGN PATENT DOCUMENTS

| | | |
|---|---|---|
| CN | 1486473 A | 3/2004 |
| CN | 1754508 A | 4/2006 |

* cited by examiner

*Primary Examiner* — Shahid K Khan
(74) *Attorney, Agent, or Firm* — Laurence Greenberg; Werner Stemer; Ralph Locher

(57) ABSTRACT

A method operates an image system of a medical imaging modality in which a patient data record of a patient is processed. A workflow for an examination is selected from a set of workflows on the basis of an examination specification of the patient data record. Wherein each workflow contains comprises a selection from a set of functions which are carried out in a specific temporal sequence.

9 Claims, 3 Drawing Sheets

METHOD FOR OPERATING AN IMAGE SYSTEM OF A MEDICAL IMAGING MODALITY AND MEDICAL IMAGING MODALITY

CROSS-REFERENCE TO RELATED APPLICATION

This application claims the priority, under 35 U.S.C. § 119, of German application DE 10 2015 225 543.3, filed Dec. 17, 2015; the prior application is herewith incorporated by reference in its entirety.

BACKGROUND OF THE INVENTION

Field of the Invention

The invention relates to a method for operating an image system of a medical imaging modality and to a medical imaging modality. In particular, the medical imaging modality is a computed tomography or magnetic resonance imaging scanner, or an x-ray system.

X-ray systems have a detector for acquiring measurement data. An important constituent of digital x-ray systems is an image system which acquires, and stores, the exposure and measurement data of the detector. Usually, the image system contains a display unit and an input apparatus, by which specific values may be entered. A computer is usually used to this end. Furthermore, the image system serves to control individual parameters of the detector or of the x-ray source when examining a patient. To this end, a so-called organ program is selected by the user of the image system. A parameter data record matched to the region of the patient to be examined is usually stored in the organ program. The parameter data record usually contains a setting for the distribution and/or intensity of the x-ray beam to be employed. It also specifies how the image calculated on the basis of the measurement data should be depicted. By way of example, specific contrast values are stored such that, for example, bones are depicted with a specific color.

In order to be able to undertake a number of very different examinations by the same image system, the latter must provide a broad spectrum of different functions for the user. Here, a user interface of the image system usually has a number of menus and submenus and/or drop-down menus, which contain commands for starting the respective function. As a consequence thereof, the user interface has a comparatively complex configuration. Thus, a user may forget to carry out a specific function when operating the x-ray system. It is also possible that the user is unaware that a specific function should always be carried out in specific cases. Furthermore, the x-ray system should be operable by users who have different responsibilities in the treatment of the patient. Thus, for example, a user may be a surgeon or a medical assistant. Thus, a configuration of the image system in which all functions are always carried out is impossible since these, for example, would have negative effects on the patient from a medical point of view. Moreover, such an x-ray system is not accepted by users.

U.S. patent publication No. 2011/0263980 A1 discloses a method for instructing a clinician. Here, patient information is called by an image system. A preset workflow and a setup parameter are selected. The image system is set on the basis of the setup parameter to carry out the selected workflow.

SUMMARY OF THE INVENTION

Therefore, the invention is based on the object of specifying a particularly suitable method for operating an image system of a medical imaging modality and a particularly suitable imaging modality, with, in particular, user acceptance being increased, development costs preferably being decreased and/or e.g. the probability of an incorrect operation being reduced.

The method serves to operate an image system of a medical imaging modality. By way of example, the medical imaging modality is a computed tomography scanner, in particular with a gantry or a C-arm, a radiography system or fluoroscopy system, or magnetic resonance imaging scanner. An image of a patient or a region of the patient is created by means of the medical imaging modality during operation, in particular a fluoroscopy image or radiography image. The image system controls the recording and/or evaluation of the image created by a detector of the imaging modality. The image system itself has, in particular, a display apparatus, for example a screen, and, preferably, an input apparatus, for example a keyboard or mouse. Expediently, the image system comprises a computer, preferably a PC or a handheld computer, for example a notebook or tablet computer. Preferably, a findings-relevant region of an organ of the patient is acquired in an x-ray image by the medical imaging modality, with the control and evaluation of the image data (x-ray image, image) and the display with a specific layout being carried out by means of the image system.

A patient data record of a patient is processed by the method, for the purposes of which e.g. values of the patient data record are modified and/or created. The patient data record has an examination specification, by which an examination, which is to be carried out by the medical imaging modality, is specified. By way of example, the examination specification is predetermined by a diagnosing medical practitioner and was generated in an independent, medical or diagnostic method. A workflow for the examination is selected on the basis of the examination specification, with a set of different workflows being provided by the method. Each workflow serves for user guidance, i.e. for guiding a user (operator) operating the medical imaging modality. Each workflow has a selection from a set of functions and the workflows differ from one another in an expedient manner. Here, at least two different workflows are present. In particular, the number of workflows in the set of workflows is less than or equal to the number of different examination specifications which are to be expected when operating the medical imaging modality. In particular, the workflows are adapted to different medical indications and have, dependent thereon, the respectively necessary functions.

As soon as the workflow was selected, the functions assigned to this workflow are carried out in a specific temporal sequence. Here it is possible, for example, that two different workflows only differ in the temporal sequence but contain the same functions. A value of the patient data record is created or modified by use of the functions themselves, at least by use of one of the functions. In particular, at least one of the functions is assigned to each value of the patient data record, wherein the associated value is created or modified by use of this function. Preferably, the image of a patient, in particular the fluoroscopy image, is stored in the patient data record by use of at least one of the functions.

The use of the workflows for the user guidance facilitates merely the functions required for the desired examination being carried out; this is determined on the basis of the examination specification. In so doing, it is moreover possible to preclude functions which are not relevant to the examination from not being carried out, increasing the user acceptance. There is a user guidance by the workflows, with the workflows preferably differing between individual clinical segments. Here, these differ e.g. by the degree of complexity, i.e., in particular, the number of functions comprised by each workflow. The assignment to each clinical segment is carried out, in particular, by the examination specification.

What is further ensured is that a function required in a specific examination is always carried out. Hence, the susceptibility to errors is reduced or an incorrect operation is essentially precluded. By way of example, an assignment to a specific body half is not required in the case of an x-ray recording of the heart of the patient, whereas such an assignment is required e.g. in the case of an x-ray recording of a hand or a leg. In this case, one of the functions is e.g. the assignment of the x-ray image to a specific body half, with, in particular, the workflow in which the examination specification requires an x-ray image of the heart not having this function. Here, a value of the patient data record which specifies the body half is, in particular, filled or modified by means of the function, with the value e.g. being a constituent of possible metadata of the x-ray image.

All that is required for training the medical imaging modality for different uses is to provide the set of workflows suitable for use. Hence, it is only necessary to define the selection of the functions and the sequence thereof. Complete reworking of a possible program for carrying out the examination is not required, which is why production costs are reduced. Moreover, adapting the workflows is possible in a comparatively uncomplicated manner.

Preferably, the workflows of different clinical segments have many similarities, which are usually temporally outside of the examination phase of the patient, i.e. the actual examination thereof. However, there are clear differences during the actual examination phase, i.e. the actual examination. By way of example, the medical imaging modality must be positioned depending on the region of the patient to be examined; thus, for example, the patient needs to be placed onto a couch in the case of specific examinations and said couch needs to be positioned accordingly in relation to the detector or the radiation source of the medical imaging modality, provided these are present. By contrast, in other examinations, it is necessary for the distance between the detector and/or the radiation source and the patient to be adjusted.

On account of the workflows, only a comparatively small number of functions of each workflow need to be changed between the individual clinical segments. In other words, a workflow of one clinical segment may be used for a further clinical segment, with only a few, specific functions needing to be removed or replaced. Hence, the production costs of the medical imaging modality are reduced.

Preferably, the workflows are created independently of the respective medical imaging modality, which is why the complete clinical breadth and also the complexity of the operation thereof are covered by use of the workflows, independently of the specific medical imaging modality. Consequently, the producer of different medical imaging modalities is able to develop a single image system and use the latter with very different medical imaging modalities. In so doing, it is only necessary to adapt or delete a comparatively small number of functions per workflow, with a new workflow being created in each case. Moreover, firstly, a training period is relatively short for users of different imaging modalities on account of the workflow. Furthermore, differences are hardly perceivable by the user due to the comparatively large number of equal functions between the individual workflows, increasing acceptance.

By way of example, the temporally successive function is called in at least one workflow of the set of workflows when the temporally preceding function is completed. The temporally first function of the workflow is in this case preferably carried out once the workflow was selected or once the workflow was started by any other means. Alternatively, or in combination therewith, at least one of the workflows is carried out in such a way that the temporally successive function is called on the basis of a user input. In other words, a user input is initially captured after completing one of the functions and, depending on the user input, the temporally successive function is carried out. The workflow is, in particular, completed provided that the temporally last function of the workflow was carried out. By way of example, some of the functions in a workflow of the set of workflows are carried out when the respective temporally preceding function was completed. The remaining part of the functions is only started when a user input corresponding to the respective function was acquired. As a consequence of this, comparatively rapid working through of the workflow is facilitated on the one hand, depending on the function carried out. On the other hand, there is e.g. a comparatively long period of time available for providing information for the user or for entering specific data, to the extent that this is required, with this period of time being terminated by means of the respective user input.

Preferably, the examination specification is queried from an radiology information system (RIS). As a consequence thereof, the processing of the patient data record is simplified. By way of example, the patient data record is queried from the RIS system. After the processing of the patient data record has been completed, the latter is stored e.g. in a picture archiving and communication system (PACS) and made available there to further systems or users.

In particular, the patient data record contains the image of the patient created by means of the medical imaging modality. By way of example, the patient data record contains a patient ID, which preferably comprises a generic number and/or the name of the patient and, in particular, his address. The patient ID is suitably likewise stored in the RIS system. In this manner, an assignment of the examination specification to the respective patient is facilitated there. In an alternative thereto, the patient ID is queried. By way of example, this is carried out by means of a function such that the patient data record is complemented by the patient ID. By way of example, the query of the patient ID is carried out by means of a user input, preferably provided the medical imaging modality is not coupled to an RIS system by signal-technical means. In other words, the workflow or, in particular each set of workflows, comprises a function in this case, by means of which an entry of the patient ID is facilitated. By way of example, the ID is read by means of a card reader from a memory chip card. In an alternative thereto, e.g. a barcode which, in particular, is imaged on a card is scanned. Preferably, the assignment of the barcode to an ID is carried out with a separate database.

By way of example, the set of functions is provided depending on an external parameter. In other words, the overall number of functions is restricted depending on the external parameter. The restriction is always such that a certain set of functions corresponds to the external parameter. By way of example, the external parameter is matched to the medical imaging modality such that only functions relevant to the respective medical imaging modality are provided. What this facilitates is using one image system when producing very different medical imaging modalities or using the image system for a further medical imaging modality. As a consequence thereof, the production costs of the medical imaging modality are reduced due to the reduced development costs.

Alternatively, or in combination herewith, the external parameter is defined dependent on a licensing fee, which is why the various functions are made available to the user depending on a specific licensing fee. What this facilitates is the production of a different number of medical imaging modalities which only differ in the set of functions provided to the user. Therefore, no new development of different medical imaging modalities is required, with the product portfolio of the producer comprising a comparatively large number of different devices.

By way of example, the external parameter is predetermined on part of a user. This facilitates an adaptation of the medical imaging modality to the respective use. By way of example, certain functions are not required in a comparatively small clinic or in an individual practice, although these are otherwise required in the case of a comparatively large clinic and, hence, a comparatively large patient throughput. Hence, the complexity of the workflows is adjustable by the external parameter, which e.g. takes place in an initial initialization of the medical imaging modality. In this manner, workflows are simplified, with functions that are not required being omitted.

Particularly preferably, the set of functions contains a function by which a selection of an organ program is carried out. In other words, a function for selecting the organ program is made available. A parameter set of the imaging modality is set by use of the organ program. In other words, the organ program contains a parameter set for setting the imaging modality. Here, certain settings of the detector and/or a radiation source of the imaging modality are adapted on the basis of the parameter data record. Alternatively, or in combination herewith, the organ program contains specific settings, on the basis of which the image created by means of the measurement values of the detector is modified. In particular, a contrast and/or an exposure time of the detector is set on the basis of the parameter data record. In particular, the organ program is a collection of parameters for the x-ray recording in a strict sense.

Alternatively, or in combination herewith, a function for image post-processing is provided. By means of thereof, there is, for example, a specific selection of a region of the image and/or a brightness and/or contrast adaptation. Preferably, a user input is acquired, on the basis of which the image post-processing is carried out. Particularly preferably, a function for entering patient data is provided. By way of example, the patient data comprise an address, an age or a weight of the patient. In conclusion, provision is preferably made of a function by means of which a value of the patient data record is modified or created. Particularly preferably, provision is further made of a function, by means of which the patient data record is stored in the PACS as soon as the examination is complete. In particular, this function is carried out at the end of each workflow. In other words, each workflow of the set of workflows comprises this function.

By way of example, after the workflow has started, it is only completed when all functions have been carried out. In other words, each individual function of the selection is carried out in the specific temporal sequence after starting the workflow, wherein, preferably, all functions are carried out successively in time. As soon as the workflow was selected on the basis of the examination specification, the case where a specific function is not carried out is precluded. Hence, an incorrect adaptation of the patient data record is not possible. Therefore, the operation of the medical imaging modality by users who have comparatively little responsibility and/or who are not trained for the medical imaging modality is facilitated.

The set of workflows has a workflow containing a function block. The function block itself has a second selection of functions. The second selection of functions is free, which is why the user can carry out these functions independently of a specific temporal sequence. In other words, the function block allows the user to select specific functions from the second selection of functions, with no further prescriptions being present. Nor is it necessary for the user to carry out all functions of the second selection. By way of example, the second selection equals the set of functions or is a subset thereof. Preferably, in addition to predefined workflows, there is the option for the user to "break out" of the current workflow on account of the function block and to select additional functions from the provided function block. The workflow expediently has further functions which are not a component of the function block.

In particular, the function block is terminated when a specific function or specific user input occurs. By way of example, such a workflow is carried out by a specific clinical segment, preferably by a surgeon. In this way, the user is able to select the required functions depending on current medical requirements, particularly in the case where the examination is a non-standard examination. Here, the function block expediently comprises all possible functions which may possibly be required. In other words, the second selection is adapted in such a way that those functions corresponding to the examination are selectable. In particular, the second selection comprises functions, by means of which roadmap, fluoroscopy or single shot x-ray methods may be carried out alternately during an examination. Expediently, the workflow comprises further functions which, however, are mandatory, for example storing the patient data record in the PACS or the function for selecting the organ program. In conclusion, the function block contains the second free selection of functions, wherein the function block is terminated by means of a user input or by carrying out a specific function. For termination, it is not necessary for all functions contained in the function block to be carried out. Moreover, no specific temporal sequence is prescribed.

Particularly preferably, the functions are subdivided into subgroups, wherein each workflow contains at least one function from each subgroup. In particular, a "patient acquisition" ("patient registration", "preparation") subgroup is formed. This subgroup preferably has a function by which a patient ID is acquired. Preferably, a further "image creation" ("examination") subgroup is formed. By way of example, the latter has a function by means of which a live image of a body part of the patient to be irradiated is created. Alternatively, or in combination therewith, this subgroup has a function for creating a certain number of images, i.e. a function for creating a series recording. Preferably, an "image processing" ("finalizing") subgroup is formed. In particular, this subgroup has a function for post-processing the created image. By way of example, this subgroup comprises a function by means of which the created image is displayed, in particular by means of the display apparatus of the image system. Suitably, this subgroup contains a function by means of which e.g. a measurement of specific properties depicted by means of the created image takes place, for example a measurement of the length of a depicted bone. Preferably, the "patient acquisition" subgroup or the "image processing" subgroup comprises a function by means of which examination images already created in a previous examination are loaded and/or displayed. By way of example, an "image archiving" subgroup is formed. Preferably, this subgroup comprises a function by means of which the image and/or the patient data record is stored. Here, there is, for example, a function for transmitting the patient data record/image to the PACS, a function for printing the patient data record/image of the patient and/or a function for storing the patient data record/image of the patient on an external medium, such as e.g. a CD, a DVD or a USB stick.

Preferably, a workflow which is adaptable on part of the user is provided. In other words, the user is able to adapt at least one workflow of the set of workflows, wherein e.g. the selected functions and/or the sequence thereof may be modified. In other words, the set of workflows is not only predetermined on part of the manufacturer. Rather, an adaptation of the workflow is also facilitated during the operation of the medical imaging modality. By way of example, the adaptation is only possible if the user has a certain authorization level. In other words, the adaptation is carried out depending on the authorization level. Preferably, the set of workflows has at least one workflow which is not adaptable on part of the user. This is, in particular, a so-called "default setting", which is predetermined on part of the manufacturer. By way of example, this workflow may be copied and the copy may be adapted by the user. Firstly, this increases flexibility. Secondly, an inhibition threshold of the user in relation to change in the workflow is reduced since said user is always able to use the workflow predetermined on part of the manufacturer.

The medical imaging modality has an image system which is provided and configured to carry out a method for operating an image system of a medical imaging modality in which a patient data record of a patient is processed, wherein a workflow for an examination is selected from a set of workflows on the basis of an examination specification of the patient data record, wherein each workflow comprises a selection from a set of functions which are carried out in a specific temporal sequence. In particular, the medical imaging modality is suitable herefor. The configurations and developments explained in conjunction with the method should be transferred analogously to the medical imaging modality, and vice versa.

By way of example, the medical imaging modality has a computed tomography or magnetic resonance imaging scanner or comprises an x-ray system. By way of example, the image system is a computer, a handheld computer, such as a notebook or tablet computer. Preferably, the medical imaging modality, in particular the image system, contains an editor for processing the workflows. Here, processing the workflows on part of the user is rendered possible, with, preferably, at least one workflow which is not modifiable on part of the user being provided. Preferably, an adaptation of an organ program is facilitated by the editor. In particular, a detector and/or a radiation source of the medical imaging modality is set by the organ program. The medical imaging modality preferably contains an organ program which is not modifiable on part of the user. As a consequence thereof, it is always possible to carry out an organ program predetermined on part of the manufacturer, which is why, in the case of a possible incorrect operation of the editor, operation of the medical imaging modality is always rendered possible, with use being made of the workflow predetermined on part of the manufacturer and the organ program predetermined on part of the manufacturer.

On account of the option for processing both the workflow and the organ program, it is only required, both on part of the manufacturer and on part of the user, to learn the operation of a single editor or to be trained in such a program. Hence, the costs for training are reduced. Also, operation is simplified. Preferably, the editor contains an option for so-called RIS matching, in which a specific general case is assigned to a specific organ program. In particular, this is carried out by means of the examination specification, which is adapted accordingly.

Preferably, the workflows/the organ programs are processed by means of incremental improvement. Here, changes possibly undertaken on part of the user are recorded for example after carrying out a workflow and/or an organ program and stored after completion of the workflow. In other words, the workflow predetermined on part of the manufacturer or the organ program predetermined on part of the manufacturer is carried out first, with changes on part of the user being possible when this workflow or organ program is carried out. The changes are recorded and a copy of the original workflow or organ program is created after completion of the workflow or the organ program, with use being made of the values modified by the user. When the same workflow or the same organ program is carried out again, use is made of the modified workflow or the modified organ program. Preferably, adjustment options are once again available to the user when the workflow or the organ program is carried out again such that, firstly, parameters possibly entered incorrectly in a preceding run may be corrected. Furthermore, a further improvement by means of an input of new parameters on part of the user is facilitated. Here, it is preferably always the respectively modified workflow or the modified organ program that is stored.

Other features which are considered as characteristic for the invention are set forth in the appended claims.

Although the invention is illustrated and described herein as embodied in a method for operating an image system of a medical imaging modality and a medical imaging modality, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Parts corresponding to one another have been provided with the same reference signs in all figures.

Figure 1:
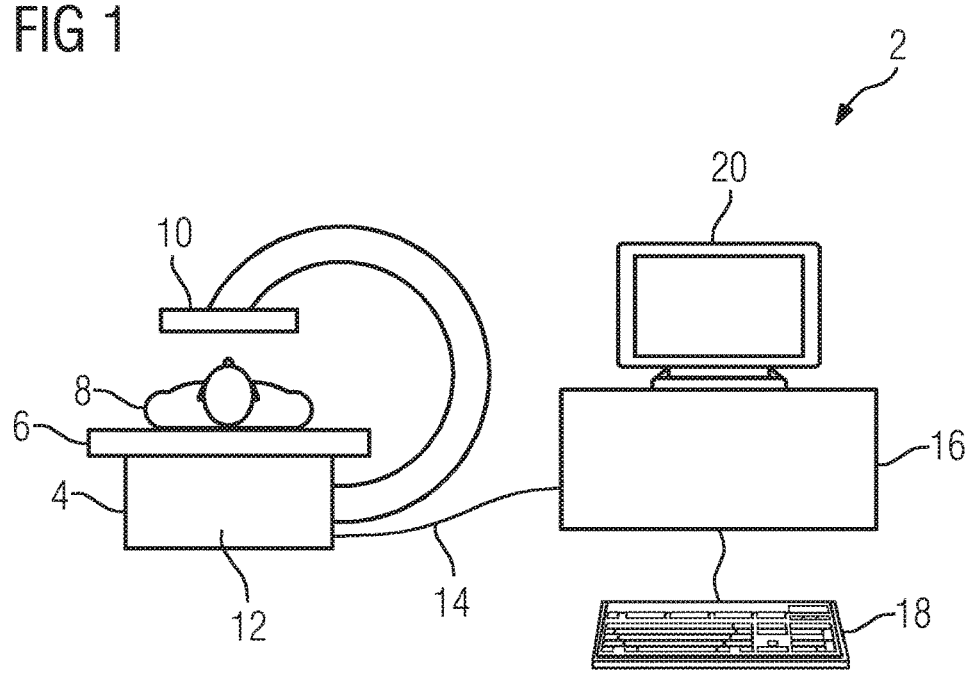
FIG. 1 is an illustration of a medical imaging modality containing an image system.

Referring now to the figures of the drawings in detail and first, particularly to FIG. 1 thereof, there is shown, in a schematically simplified manner, a medical imaging modality 2 comprising an x-ray system 4. The x-ray system 4 has a table 6, on which a patient 8 is positioned during operation. An x-ray tube 10, by which x-ray radiation for irradiating the patient 8 is produced, is situated in a vertical direction over the table 6 and over the patient 8. The x-ray radiation is acquired by a detector 12, which is positioned below the table 6 in the vertical direction. By a signal line 14, the x-ray system 4 is coupled to an image system 16, the latter having an input apparatus 18 in the form of a keyboard and a mouse not depicted in any more detail, and a display apparatus 20 which is configured in the style of a computer monitor. Furthermore, the image system 16 contains a non-illustrated a microprocessor and electronic memory components, and also further electric and/or electronic components.

Figure 2:
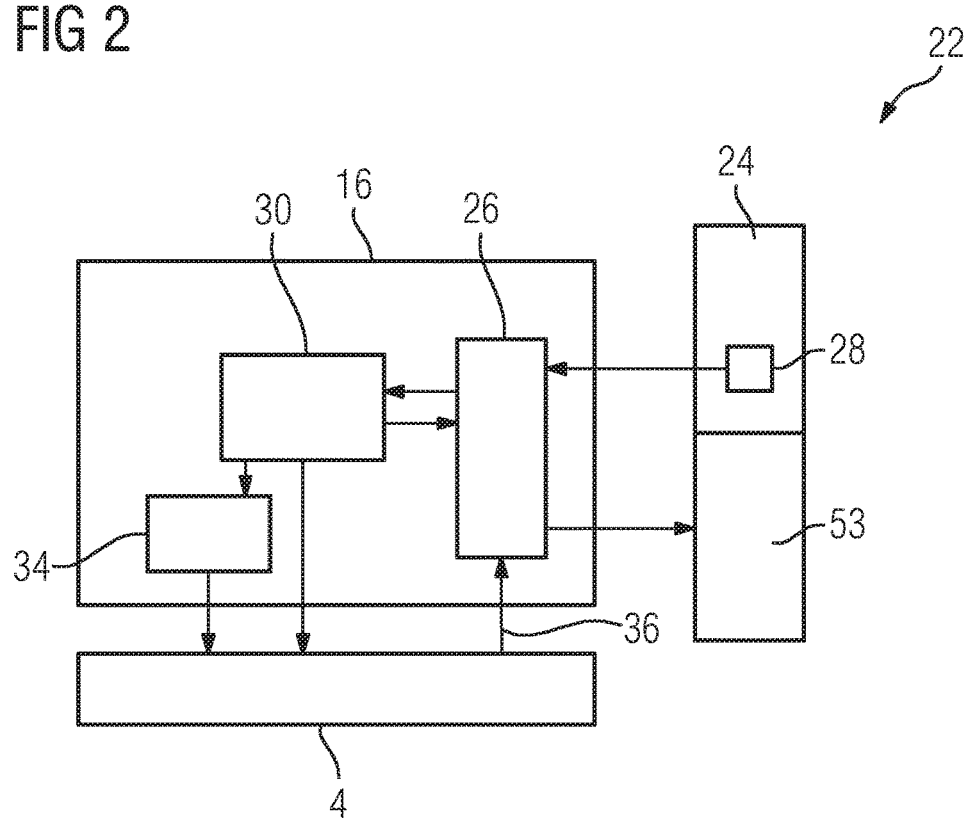
FIG. 2 is a block diagram illustrating a method for operating the image system, in which a workflow is selected.

FIG. 2 schematically depicts a method 22 for operating the image system 16, which is coupled to an RIS system 24. In the image system 16, there is a patient data record 26 which, for example, was queried/loaded from the RIS system 24. Alternatively, the patient data record 26 was queried from a further system (not depicted here) or created by means of the image system 16 itself. An examination specification 28 is called from the RIS system 24 and stored in the patient data record 26. Alternatively, the patient data record 26 is queried/loaded with the already available examination specification 28 from the RIS system 24.

Figure 3:
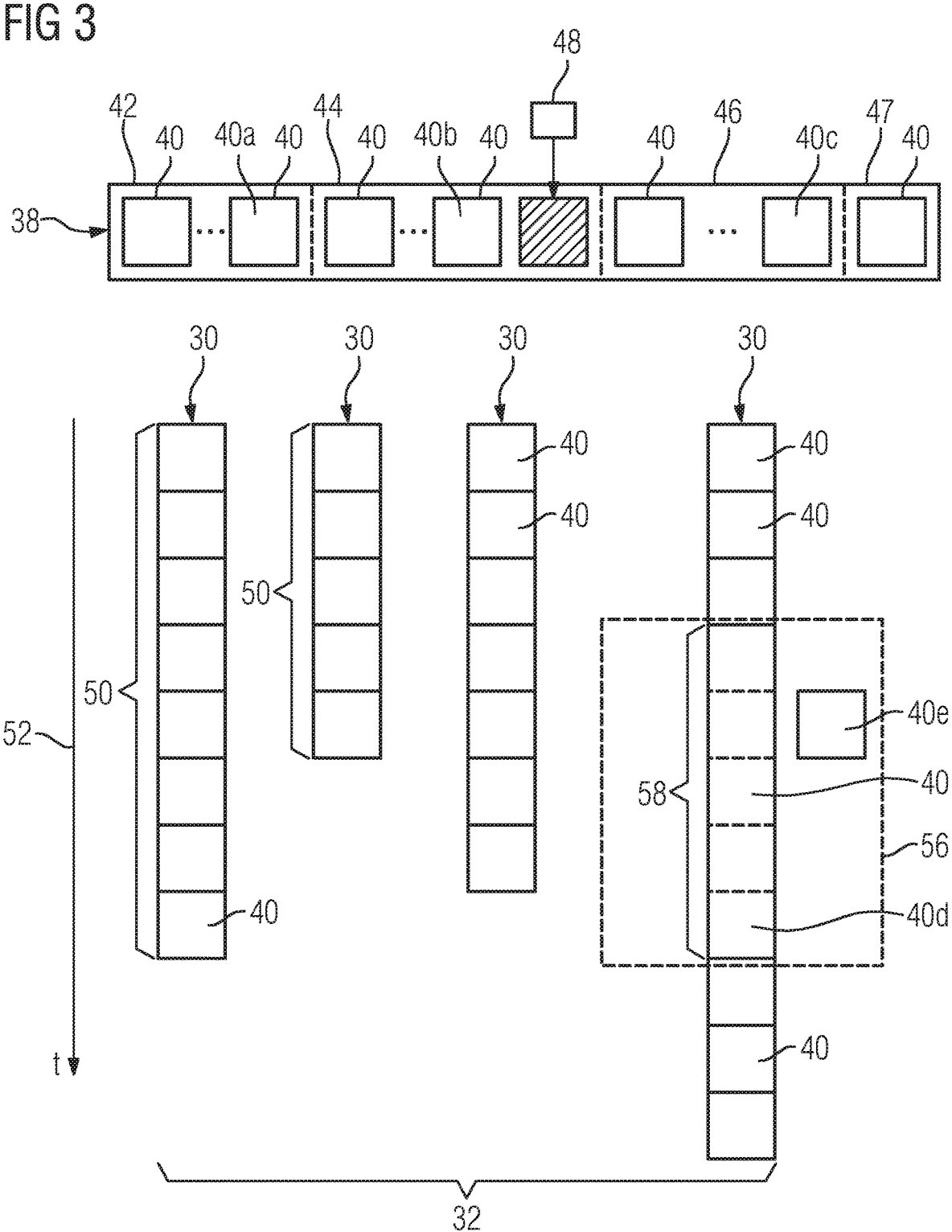
FIG. 3 is an illustration showing different workflows with, in each case, a different selection of functions.

A workflow 30 of a set 32 of workflows depicted in FIG. 3 is selected on the basis of the examination specification 28, wherein the set 32 contains e.g. four such workflows 30. Each one of the workflows 30 corresponds to one of the examination specifications 28, which is why a number of workflows 30 corresponding to the number of different examination specifications 28 is stored. An organ program 34, by means of which the x-ray system 4 is controlled, is selected by the workflow 30. Furthermore, the x-ray system 4 is directly influenced by the workflow 30, wherein e.g. the x-ray tube 10 and/or the table 6 are displaced. The image data 36 created by means of the x-ray system 4 are stored in the patient data record 26 by means of the workflow 30 and the patient data record 26 stored in the RIS system 24.

The image system 16 has a set 38 of functions 40 shown in FIG. 3. The set 38 contains all functions 40 by which there could be a control of the medical imaging modality 2 and a control of further medical imaging modalities, in which, for example, the x-ray system 4 is modified or replaced. The set 38 is subdivided into a "patient acquisition" subgroup 42, an "image creation" subgroup 44, and an "image processing" subgroup 46 and an "image archiving" subgroup 47. In other words, the functions are subdivided into the subgroups 42, 44, 46, 47.

The "patient acquisition" subgroup 42 has a function 40a for entering patient data. When carrying out the function 40a for entering patient data, a user input on part of a user by means of the input system 18 is required. The "image creation" subgroup 44 has a function 40b for selecting the organ program 34. Here, for example, the organ program 34 corresponding to the examination specification 28 is selected. By way of example, in the case of an examination specification 28 of a lung, a control data record for the x-ray system 4, corresponding to a lung, in the form of the respective organ program 34 is selected. To that effect, in the case of an examination specification 28 of an x-ray recording of a hand, an organ program 34 corresponding thereto is selected, with an exposure time and a contrast being modified in the organ program. In particular, each workflow 30 contains the function 40b for selecting the organ program 34. The "image processing" subgroup 46 has a function 40c for image post-processing, by which, for example, there is a manual adaptation of the brightness or contrast of the image data 36 by the input system 18.

The set 38 of the function 40 is restricted on the basis of an external parameter 48. In the example, one of the functions 40 of the "image creation" subgroup is removed from the set 38. The external parameter 48 corresponds to a license or license key. Hence, the set 38 of the available functions 40 changes if the external parameter 48 is changed.

The set 32 of workflows 30 is formed on the basis of the set 38 of the functions 40, with each workflow 30 having a selection 50 from the set 38 of functions 40. Here, the functions 40 are arranged in a specific temporal sequence 52. The selection 50 of different workflows 30 differs in terms of the functions 40 used to form the respective workflow 30 and/or in terms of the sequence in which the individual functions 40 are arranged. Each workflow 30 has at least one of the functions 40 from the "patient acquisition" subgroup 42 and one of the functions 40 from the "image creation" subgroup 44, and one of the functions 40 from the "image processing" subgroup 46. However, none of the workflows 30 has the function 40 which is locked on account of the external parameter 48. Each workflow 30 has a function from the "image archiving" subgroup 47 for storing the patient data record 26 in a PACS 53 (FIG. 2). In particular, in the temporal sequence 52, such a function is the last function 40 of each workflow 30.

Figure 4:
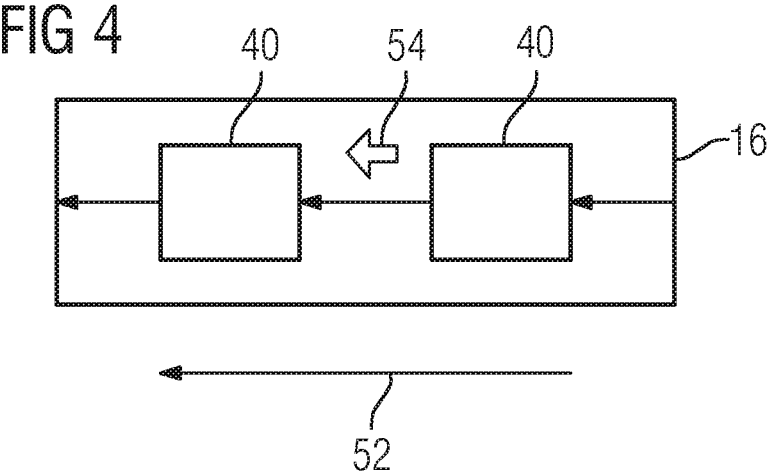
FIG. 4 is a block diagram showing an output on a display unit of the image system.

As soon as one of the workflows 30 was started, all functions 40 of the respective workflow 30 are carried out successively in the temporal sequence 52. Here, the temporally successive function 40 is e.g. started when the temporally preceding function 40 was completed. In an alternative thereto, a user input 54, which is effected by means of the input system 18, is acquired, at least in a number of functions 40. The temporally successive function 40 is only called once this user input 54 was acquired, as depicted in FIG. 4. By way of example, the display apparatus 20 is used here to display an arrow or a button, on which a user clicks with the mouse of the input system 18.

One of the workflows 30 has a function block 56 which contains a second selection 58 of functions 40. The functions 40 in the function block 56 do not have a fixedly predetermined temporal sequence 52. Furthermore, it is not necessary for all functions 40 of the second selection 58 to be carried out for the purposes of terminating the function block 56. Rather, the function block 56 is terminated and the temporally successive function 40 is called if a specific function 40d is carried out or if a user input is acquired by a function 40e for acquiring the user input.

Figure 5:
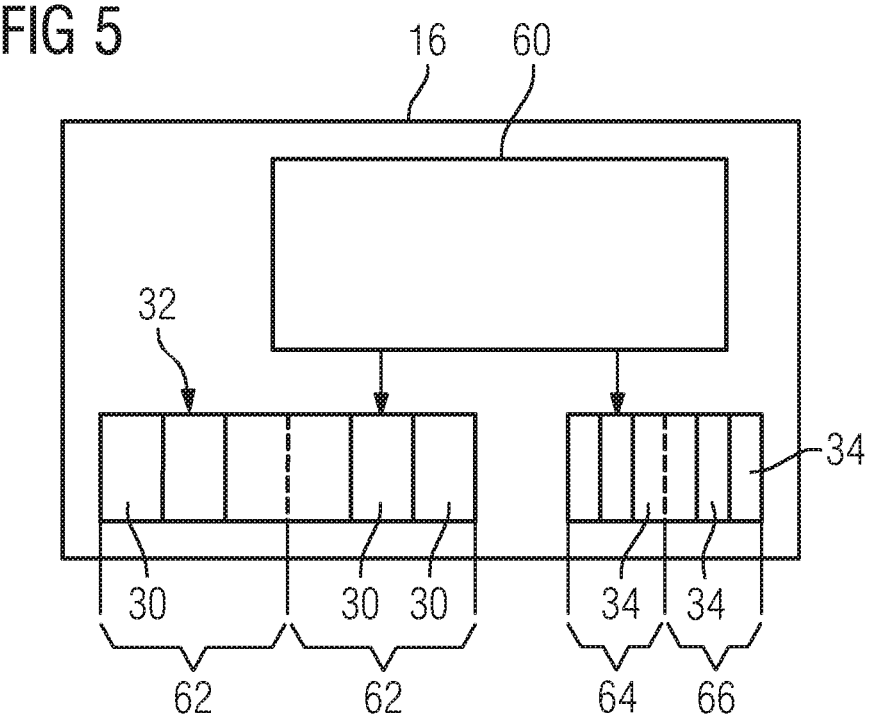
FIG. 5 is a block diagram of an editor for processing the workflows.

The image system 16 has an editor 60 depicted in FIG. 5, by means of which workflows 30 of the set 32 of workflows 30 are adaptable on part of the user. The adaptation only occurs if the user has a certain authorization level. The set 32 of workflows 30 is subdivided into two subsets 62. Only the workflows 30 of one of the subsets 62 are adaptable on part of the user by means of the editor 60. By contrast, the workflows 30 of the remaining subset 62 are predetermined on part of the manufacturer and serve as a standard. Moreover, an adaptation of the organ programs 34 is facilitated by means of the editor 60, with two different types of organ programs 34 once again existing here as well, namely the organ programs 64 which are modifiable on part of the user and the organ programs 66 predetermined on part of the manufacturer. The organ programs 66 predetermined on part of the manufacturer are not modifiable by means of the editor 60. An alternative to the editor 60, or a development thereof, is that a change in the temporal sequence 52 or a change of parameters is recorded in each workflow 30 and, when the respective workflow 30 is terminated, this change is stored in the respective workflow 30. In this manner, training of staff for operating the editor 60 is substantially not required.

The invention is not restricted to the exemplary embodiment described above. Rather, other variants of the invention may also be derived herefrom by a person skilled in the art, without departing from the subject matter of the invention. In particular, all individual features described in conjunction with the exemplary embodiment are further also combinable with one another in a different way, without departing from the subject matter of the invention.

The invention claimed is:

1. A method for operating an image system of a medical imaging modality in which a patient data record of a patient is processed, which comprises the steps of:
    selecting a workflow for examination from a set of workflows for user guidance on a basis of an examination specification of the patient data record, each of the workflows having a selection from a set of functions which are carried out in a specific temporal sequence, and the workflow having a function block with functions that are freely selectable by a user, the function block being terminated by means of user input or by means of carrying out a specific function;
    wherein the function block enables the user to select all of the functions of the function block to be part of the workflow and the function block enables a user to select less than all of the functions of the function block to be part of the workflow; and
    wherein the functions in the function block are initially defined in the function block, and at least some functions in the workflow are temporally located before the function block.

2. The method according to claim 1, which further comprises calling a next function in time on a basis of the user input.

3. The method according to claim 1, which further comprises querying the examination specification from a radiology information system.

4. The method according to claim 1, which further comprises making available the set of functions in dependence on an external parameter.

5. The method according to claim 1, which further comprises providing at least one of a function for selecting an organ program, a function for image post-processing or a function for entering patient data.

6. The method according to claim 1, which further comprises subdividing the functions into subgroups, wherein a patient acquisition subgroup, an image creation subgroup, an image processing subgroup, and an image archiving subgroup are formed, and wherein each of the workflows has at least one function from each of the subgroups.

7. The method according to claim 1, which further comprises providing at least one workflow which is adaptable on part of a user.

8. A medical imaging modality, comprising:
    an image system for a medical imaging modality in which a patient data record of a patient is processed, said imaging system programmed to select a workflow for an examination from a set of workflows for user guidance on a basis of an examination specification of the patient data record, each of the workflows having a selection from a set of functions which are carried out in a specific temporal sequence, and the workflow having a function block with functions that are freely selectable by a user, the function block being terminated by means of user input or by means of carrying out a specific function;
    wherein the function block enables the user to select all of the functions of the function block to be part of the workflow and the function block enables a user to select less than all of the functions of the function block to be part of the workflow; and
    wherein the functions in the function block are initially defined in the function block, and at least some functions in the workflow are temporally located before the function block.

9. The medical imaging modality according to claim 8, further comprising an editor for processing the workflow and an organ program.

* * * * *